Figure 2:
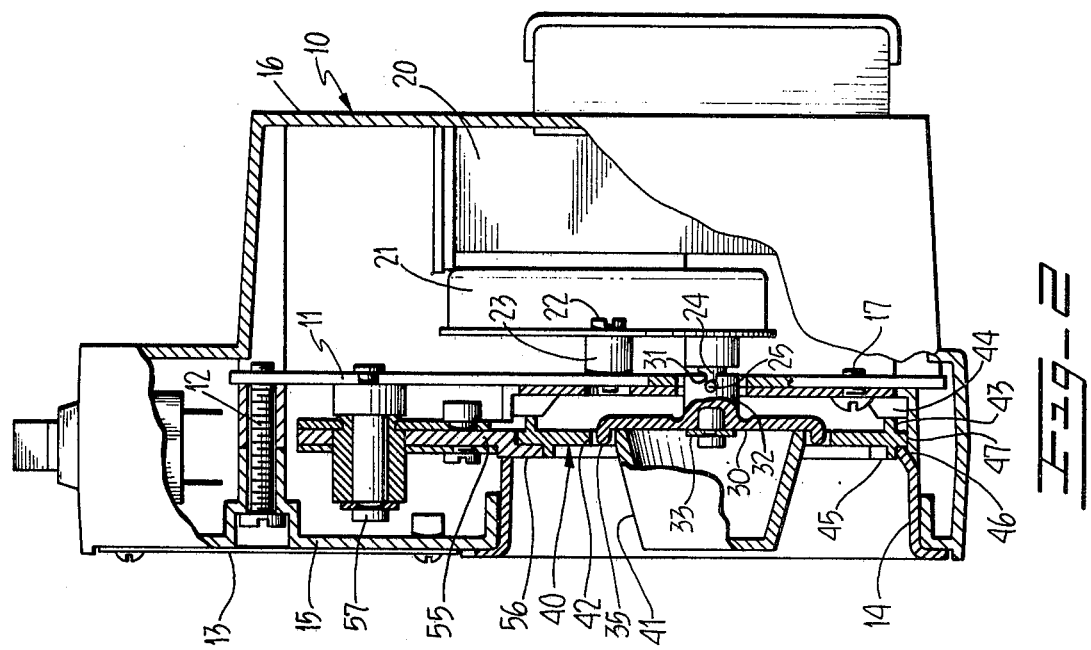

United States Patent [19]

Lundquist

[11] 4,091,810
[45] May 30, 1978

[54] METHOD FOR INTRAVENOUS FEEDING OF A PATIENT

[75] Inventor: Ingemar H. Lundquist, Oakland, Calif.

[73] Assignee: Valleylab, Boulder, Colo.

[21] Appl. No.: 727,294

[22] Filed: Sep. 27, 1976

Related U.S. Application Data

[62] Division of Ser. No. 627,842, Nov. 3, 1975, abandoned.

[51] Int. Cl.² .............................................. A61M 5/00
[52] U.S. Cl. ............................................... 128/214 F
[58] Field of Search .......... 128/214 R, 214 E, 214 F, 128/214.2, DIG. 12, DIG. 13

[56] References Cited

U.S. PATENT DOCUMENTS

| | | | |
|---|---|---|---|
| 3,068,817 | 12/1962 | Hamlett | 112/158 A |
| 3,625,212 | 12/1971 | Rosenberg et al. | 128/214 R |
| 3,724,282 | 4/1973 | Daman | 112/158 A |
| 3,798,982 | 3/1974 | Lundquist | 128/214 F X |
| 3,901,231 | 8/1975 | Olson | 128/214 F |
| 3,994,294 | 11/1976 | Knute | 128/214 F |

*Primary Examiner*—Dalton L. Truluck
*Attorney, Agent, or Firm*—Flehr, Hohbach, Test, Albritton & Herbert

[57] ABSTRACT

Method for intravenous feeding of a patient by a pump and a pump actuator which is provided with readily insertable and removable cams which control the number of pump strokes per unit of time and also the amount of intravenous fluid injected by each stroke in accordance with a prescription of intravenous fluid placed in a container. A predetermined prescription of intravenous fluid is prepared and placed in a container. The container and a cam which is tailored to the requirements of the prescription in the container is delivered to the patient. The cam is placed on the pump actuator. The container is connected to the pump and the pump is connected to a vein of the patient. The pump actuator is operated by the use of the cam to operate the pump to supply the prescribed intravenous liquid in the container to the patient in accordance with the prescription.

2 Claims, 2 Drawing Figures

U. S. Patent  May 30, 1978  4,091,810

METHOD FOR INTRAVENOUS FEEDING OF A PATIENT

This is a division, of application Ser. No. 627,842 filed Nov. 3, 1975, now abandoned.

BACKGROUND OF THE INVENTION

In recent years there has been a very rapidly growing use of forcibly pumping blood or various feeding solutions into the veins of a patient by means of positively operated pumping devices. Such devices are much more accurate in the delivery of liquid to the patient than the older feeding by gravity only. Often, the intravenous feeding requires the delivery of very small amounts from 0.5 milliliters per hour up to as much as 500 to 1500 milliliters per hour (the equivalent of about 16 and 48 ounces, respectively, per hour). At the lower rates of feed there is frequent clogging of the delivery tube or needle which delivers the material into the vein of the patient and there is also considerable inaccuracy in the amount delivered over a period of time. This requires frequent checking of the gravity feed of such liquid to a patient by a nurse, or other qualified person. The present invention relates to an actuating device for a pump whereby the number of strokes in a given unit of time, such as one minute, and the length of the stroke (which is equivalent to saying the amount of fluid per stroke) is variable over a wide range. In this respect, the present invention comprises a big improvement over the pump actuator shown in my prior U.S. Pat. No. 3,798,892, issued Mar. 26, 1974, as it is not only much smaller and therefore more easily portable, but is also more readily adjusted by the nurse or doctor in charge of administering the fluid to the patient. It is obvious that such a driver or actuator, must be positive in its operation and must be readily adjustable to provide a wide range of delivery. The device of the present invention is more practical than that of my former patent in that it relieves the nurse of doctor on the floor from having to readjust the actuator each time it is used. It is a growing development in the field of medicine, particularly in the better hospitals, to prepare the material to be delivered in the hospital pharmacy and deliver it properly measured and marked with proper operating instructions to the floor where the patient is located so that the nurse does not have to take time to do a lot of figuring or adjusting of equipment. Such devices are disclosed in my copending applications, Ser. No. 514,219, for Measured Volume Drug Adminstration Device, filed Oct. 11, 1974, now U.S. Pat. No. 3,965,897 or Ser. No. 538,372, entitled Drug Dispenser for use with Intravenous feeding pump, filed Jan. 3, 1975, now U.S. Pat. No. 3,976,068. In suc hospitals, using the present invention, the pharmacy would also send to the nurses station the proper cam to be used for the pump actuator so that the doctor or nurse would not be required to determine which cam should be used and what the length of stroke of the pump actuating cam follower should be.

As indicated above, the device of the present invention includes a set of cams which are easily removable from, or inserted into, the pump actuator. Thus, an operator has merely to set the material to be fed, the necessary tubing, sterilized pump, the proper cam (all of which can be furnished by the hospital pharmacy) into the pump actuator already at the bedside, insert the needle into the patient and initiate operation of the pump actuator. All of this is done without the operator (who is often very busy) having to bother about determining the number of strokes per minute, the length of each stroke, or otherwise setting the device.

OBJECTS

It is an object of this invention, therefore, to provide a driver, or actuator, for an intravenous delivery pump which is extremely accurate in its operation and which can be more readily adjusted to provide for a very wide range of delivery volumes to a patient, than is now possible.

It is another object of the invention to provide a pump actuator which can be readily adjusted, even while in use, with the delay of only a few seconds necessary to slip one operating cam off the drive shaft and replace it by another.

It is another object of the invention to provide a method for intravenous feeding of a patient using an actuator for a pump in which the actuator has removable cams so that a cam tailored for the prescription for the patient can be provided.

These and other objects of the present invention will be apparent from the detailed specification which follows when taken in view of the drawings which are a part hereof.

DRAWINGS

Figure 1:
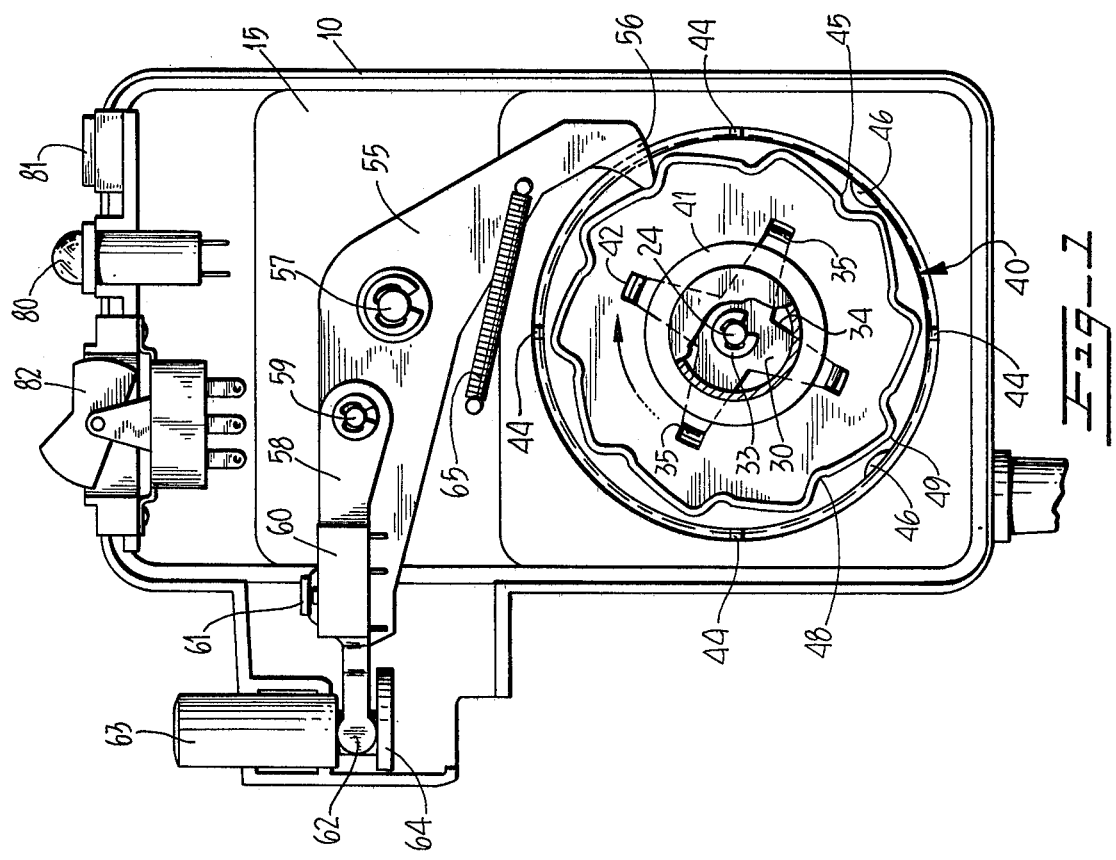

FIG. 1 is a front view, with the cover plate removed, of the device of the present invention in an operating condition; and FIG. 2 is a side view, principally in cross-section, of the device of FIG. 1.

The device of the present invention is contained within a casing 10 formed of any suitable material, such as a molded plastic shell having integral side walls, not identified. A partition plate 11, shown particularly in FIG. 2, is fastened in an intermediate location between the back 16 and a partial front mounting plate 15. This partition 11 can be held in proper position by any suitable means, such as studs 12. The partial front mounting plate 15 extends only over the upper portion of the casing and is fastened by suitable means to the back 16 by means not shown. The upper part of the casing is covered by a front face member 13 mounted on the partial front mounting plate. A cam well 14, open at the front, is attached to the partition by any suitable means, such as screws 17.

A slow speed motor 20 and its integral gear box 21 are rigidly secured within the casing 10 by any suitable means, such as stud 22 and spacer 23. The output shaft 24 from the gear box 21 faces toward the front of the device and is provided with some means, such as the pin 25, which extends through the shaft 24 and is adapted to fit within a slot 31 in the hub 32 of a spider 30. The spider 30 is held on the shaft 24 by any suitable means, such as C-ring fastener 33. The spider is provided with a plurality (four in the preferred form as shown in the drawings) of arms 34, each of which is provided at its outer end with a forwardly turned ear, or bracket, 35. It is thus seen that the operation of the motor 20 will drive the mounting spider 30 at some predetermined slow speed, such as 1 r.p.m.

A cam plate 40, preferably circular in shape, is adapted to be inserted over the drive spider 30. Preferably it has a centrally located truncated conical projection which might appear to be a hub which actually is only a handle for ease in manipulating the cam 40. The cam 40 is provided with a suitable plurality (four in the embodiment shown of slots 42 for receiving the ears 35 on the spider 30. It can be noted at this point that the cam plate 30 is not locked to the drive shaft 25 or the spider 30, but is loosely mounted thereon. It is held in the proper position by the peripheral edge 47 of the cam riding on the bottom wall of the cam well 14. The cam is held within the well by means of a pair of holding lugs 46 formed on the lower section of the circular wall of the well 14 which engage the face of the cam 40 adjacent the edge thereof and by the upper edge of the cam being held in proper position by lying behind the nose 56 of the cam follower 55 to be described shortly. The cam 40 is provided on its rear face with a circular peripheral spacer wall 43 which engages a plurality of lugs, or bosses, 44 formed on the interior face of the well 14. Thus, the cam is, in effect, centerless and is held in its proper operating position by lying against the lugs 44 of the well and behind the holding lugs 46 and the nose 56 of the cam follower arm 55.

The cam 40 is provided with a cam wall or projection 45 on its outer face. In the embodiment shown in FIG. 1, this cam face 45 has ten depressions 48, each of which is proceeded by a gradual rise 49, thus providing ten operations of the cam follower 55 in each revolution of the cam 40. The cam follower 55 is pivotally mounted on the partition plate 11 by any suitable means, such as stud 57. The follower arm 55 is provided with a forwardly offset nose 56 which, when the cam 40 and follower arm 55 are in operative position, will ride on the periphery of the cam and will lie against the outer face, thereby holding the top of the cam in its proper position. When the cam follower 55 is not rocked by the cam ridge 45, the shoulder between the main portion of the follower arm 55 and its offset nose 56 will ride upon the periphery of the cam 47, as shown in FIG. 2. However, when the nose 56 is rocked by engagement with a rise 49 of the camming section 45, the follower arm will obviously rock around its pivot 57.

In the embodiment shown, the follower arm 55 is provided with the failure alarm system described in my copending application, Ser. No. 488,581, filed July 15, 1974, abandoned in favor of application Ser. No. 635,656 filed Nov. 26, 1975, now U.S. Pat. No. 4,056,333 issued Nov. 1, 1977, and entitled Intravenous Pump Failure Alarm System. Briefly, this comprises an auxiliary arm 58 pivotally mounted on the follower 55 by any suitable means, such as stud 59. The auxiliary arm 58 carries a suitable Micro-Switch 60 mounted thereon which is engaged by a bracket 61 formed on the forward projecting arm of the follower 55. By this construction, the Micro-Switch 60 will be held in one position when the arms 58 and 55 operate together. However, when the arm 58 fails to follow the arm 55, then the switch 60 is operative to actuate an alarm system by changing the setting of the switch 61. This alarm system may comprise a signal light 80 shown at the top of FIG. 1, but obviously could also be an audible signal, or signals at the nurses station. In the preferred embodiment of the invention, both the follower arm 55 and the auxiliary arm 58 are provided with a nose 62 on their outer ends which lie between a pushbutton 63 and a bracket 64 that is loosely contained within the button 63, as shown in FIG. 1.

The actuator of the present invention is designed particularly to be operative with, or upon, the pump of the kind described in my prior U.S. Pat. No. 3,874,826, in which the bracket 64 engages the outer end of a plunger which extends within the pumping chamber (not shown) of the pump, which plunger is returned ot is inoperative position by resilient means not pertinent to this invention. The rocking of the arm 55 will depress the bracket 64 and thus push the plunger into the pumping chamber to pump liquid therefrom. At the end of the pumping stroke, the arm 55 is returned to its inoperative position by a tension spring 65 tensioned between the follower and the front plate 15 of the device. The plunger in this pump is returned to its inoperative position by some resilient means, such as a rubber sheath (not shown or described herein but which is fully explained and described in the above-mentioned patents). Since the pump is not part of this invention, it will not be further described but it will be noted that the alarm system is dependent upon the failure of the resilient means for returning the pumping plunger to its inoperative position, which may occur from a number of reasons, such as breaking of the resilient means, blockage of the supply of fluid, or the like. What is important in this connection is that the follower arm 55 of the present invention can be adapted to use the alarm system of my copending application, Ser. No. 488,581 above mentioned, and this means is shown in FIG. 1. In addition to the alarm light 80 already mentioned, it is preferred that the device of the present invention also include a jack 81 for transmitting a failure signal from the bedside of a patient to a central location, such as a nurses station. Also included would be the conventional operating switch 82 to control power to the pump actuator.

It is believed that the operation of the present device will be obvious. Briefly stated, it includes the installation of a pump, not shown, with its operating plunger against the bracket 64 and the pump placed in a suitable location adjacent the bedside of a patient. The material to be injected into the patient can be supplied to the nurses station by the hospital pharmacy, together with the particular cam designed to provide the prescribed dosage rate. In the event a saline solution or blood is to be injected together with a prescribed medication, the medication can be provided by the hospital pharmacy by using a drug injection device of the kind described in my copending application Ser. No. 514,219, filed Oct. 11, 1974, now U.S. Pat. No. 3,965,897 or Ser. No. 538,372, filed Jan. 3, 1975, now U.S. Pat. No. 3,976,068. The pump would be filled with fluid to be pumped and air driven from the system as described in said pump patent. To secure the necessary pump operation, a cam 40 will be placed in the cam well 14 by lifting the nose 56 of follower 55 away from the cam, setting the cam behind the holding lugs 46 and over the spider 30, pushing the top of the cam back against the spacing lugs 44, and then setting the nose 56 over the face of the cam. The cam is thereby held in proper operating position. The number of operation per revolution is determined by the number of rises 49 on the cam wall 45 and the length of the stroke will be determined by the depth of the depression 48 following each such rise. It is obvious that by varying the number of rises and depressions on a cam and the depth of each depression, the amount to be pumped can be controlled over wide limits. The pump can be designed for an unlimited number of different flow rates ranging betwee 0.5 milliliters per hour to 1,000 milliliters per hour. It will be understood that each separate rate of flow will require a separate cam specifically designed for that volume of operation.

When viewed as a method of providing a "fail-safe" system of intravenous feeding of a patient, it includes the steps of:

(1) the hospital pharmacy provides the nurses station with the material to be injected into the medication (and if medication is to be added to another feeding solution, that could be provided by using a power-operated drug injection device such as one of those described in the applications referred to in the preceding paragraph) and the specific cam designed to feed the solution at the prescribed rate;

(2) at the proper time the nurse or aide merely attaches the material to be injected to the pump and changes the cam in the pump actuator.

By this method a nurse's aide can be used to treat the patient, as no measurement of medication is required at that time as all material to be injected was provided by the pharmacy, and no adjustment of the pump actuator is necessary as that has also been provided by the pharmacy. It is thus obvious that much of the work that now has to be done by a nurse can be done by lesser qualified personnel as no measurements or adjustments are necessary at the patient's bedside. It also provides means whereby the time required to prepare for the intravenous feeding of a patient is materially reduced, as bedside or nurses station measurements or adjustments need no longer be made. This saving of time by floor personnel is important in many hospitals that find it impossible to find suitably trained personnel to adequately handle the patient load.

It is believed obvious that many modifications can be made in the present invention. For example, the cam plates could be rigidly secured on the drive shaft 24 by means of a locking nut or otherwise, although that would require the nurse or doctor operating the pump to lay down the cam to be used, to manually release the cam that had been in the machine, to then replace it and lock the new one on the shaft. It is believed the present embodiment makes it easier and quicker for the attendant to set the proper cam within the machine. It is also obvious that other volumes could be provided for by changing the number of cams, cam rises and depressions on the face of the cam so that volumes could be more or less than those specified. It is also believed obvious that while a continuous cam ridge 45 is preferred, that a plurality of disjointed rises could be used as well, It is also obvious that the speed above mentioned can be varied from that described and the same quantities can be pumped per hour by changing the number of lobes on the various cams and the length of each stroke by varying the distance between the top of the rise and the depth of the depression to which the cam follower 55 can fall.

I claim:

1. The method of providing for a "fail-safe" intravenous feeding of a patient which comprises:
   (a) providing at the bedside of the patient an intravenous feeding pump and a pump actuator having a readily insertable and removable cam which controls the number of pump strokes per unit of time and also the amount injected by each stroke;
   (b) preparing at a place remote from the patient and in a suitable container the proper amount of material to be injected into the veins of the patient and providing at such place a cam adapted to provide the prescribed feeding rate to the patient;
   (c) transporting the said material to be injected and the said cam to the bedside of the patient;
   (d) connecting the said container of material to be injected to said pump and placing the said cam in said actuator; and
   (e) filling the pump with material to be injected and connecting said pump to a vein of the patient.

2. In a method for intravenous feeding of a patient by a pump and a pump actuator which is provided with readily insertable and removable cams which control the number of pump strokes per unit of time and also the amount of intravenous fluid injected by each stroke in accordance with a prescription of intravenous fluid placed in a container, preparing a predetermined prescription of intravenous fluid and placing it in a container, delivering the container and a cam which is tailored to the requirements of the prescription in the container to the patient, placing the cam on the pump actuator, connecting the container to the pump, connecting the pump to a vein of the patient and operating the pump actuator by the use of the cam to operate the pump to supply the prescribed intravenous liquid in the container to the patient in accordance with the prescription.

* * * * *